(12) United States Patent
Fonseca et al.

(10) Patent No.: US 9,820,698 B2
(45) Date of Patent: Nov. 21, 2017

(54) ACTIGRAPHY METHODS AND APPARATUSES

(71) Applicant: KONINKLIJKE PHILIPS N.V., Eindhoven (NL)

(72) Inventors: Pedro Miguel Fonseca, Borgerhout (BE); Reinder Haakma, Eindhoven (NL); Ronaldus Maria Aarts, Geldrop (NL); Xi Long, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/934,255

(22) Filed: Nov. 6, 2015

(65) Prior Publication Data

US 2016/0128641 A1 May 12, 2016

Related U.S. Application Data

(60) Provisional application No. 62/076,693, filed on Nov. 7, 2014, provisional application No. 62/101,408, filed on Jan. 9, 2015.

(51) Int. Cl.
*A61B 5/02* (2006.01)
*A61B 5/00* (2006.01)
(Continued)

(52) U.S. Cl.
CPC .......... *A61B 5/7278* (2013.01); *A61B 5/0245* (2013.01); *A61B 5/0402* (2013.01);
(Continued)

(58) Field of Classification Search
None
See application file for complete search history.

(56) References Cited

U.S. PATENT DOCUMENTS

2005/0131288 A1\* 6/2005 Turner ................ A61B 5/0006
600/391
2005/0245790 A1\* 11/2005 Bergfalk .............. A61B 5/0002
600/300
(Continued)

FOREIGN PATENT DOCUMENTS

| EP | 2428159 A2 | 3/2012 |
|----|------------|--------|
| WO | 2011013132 A1 | 2/2011 |
| WO | 2014053538 A1 | 4/2014 |

OTHER PUBLICATIONS

Long et al, "Analyzing Respiratory Effort Amplitude for Automated Sleep Stage Classification", Biomedical Signal Processing and Control, vol. 14, 2014, pp. 197-205.
(Continued)

*Primary Examiner* — Ankit D Tejani

(57) ABSTRACT

An actigraphy method includes receiving a physiological parameter signal as a function of time for a physiological parameter other than body motion (such as electrocardiography or a respiration monitor), computing a body motion artifact (BMA) signal as a function of time from the physiological parameter signal (for example, using a local signal power signal, a local variance signal, a short-time Fourier transform, or a wavelet transform over epochs of duration on order a few minutes or less), and computing an actigraphy signal as a function of time from the BMA signal, for example by applying a linear transform to the BMA signal and optionally applying filtering such as median removal and/or high-pass filtering.

20 Claims, 16 Drawing Sheets

(51) Int. Cl.
    A61B 5/0245    (2006.01)
    A61B 5/0402    (2006.01)
    A61B 5/11      (2006.01)
    A61B 5/113     (2006.01)
    A61B 5/08      (2006.01)

(52) U.S. Cl.
    CPC .......... *A61B 5/0816* (2013.01); *A61B 5/1118*
        (2013.01); *A61B 5/1135* (2013.01); *A61B*
        *5/4812* (2013.01); *A61B 5/725* (2013.01);
        *A61B 5/726* (2013.01); *A61B 5/7257*
        (2013.01); *A61B 5/0809* (2013.01); *A61B*
        *5/4806* (2013.01); *A61B 5/7203* (2013.01);
        *A61B 5/7242* (2013.01)

(56) References Cited

U.S. PATENT DOCUMENTS

| | | | |
|---|---|---|---|
| 2007/0213620 A1* | 9/2007 | Reisfeld | A61B 5/0402 600/484 |
| 2009/0149770 A1* | 6/2009 | Sing | A61B 5/04017 600/544 |
| 2011/0082355 A1 | 4/2011 | Eisen et al. | |
| 2012/0302926 A1* | 11/2012 | Tanaka | A61B 5/11 600/595 |
| 2014/0088373 A1* | 3/2014 | Phillips | A61B 5/113 600/301 |

OTHER PUBLICATIONS

Karlen et al, "Sleep and Wake Classification With ECG and Respiratory Effort Signals",, IEEE Transactions on Biomedical Circuits and Systems, vol. 3, No. 2, 2009, pp. 71-78.

Pawar et al, "Analysis of Ambulatory ECG Signal", Proceedings of the 28TH IEEE EMBS Annual International Conference, 2006, pp. 3094-3097.

Pawar et al, "Transition Detection in Body Movement Activities for Wearable ECG", IEEE Transactions on Biomedical Engineering, vol. 54, No. 6, 2007, p. 1149-1152.

Pawar et al, "Impact Analysis of Body Movement in Ambulatory ECG", Proceedings of the 29th Annual International Converence of the IEEE EMBS, 2007, pp. 5453-5456.

Pawar et al, "Body Movement Activity Recognition for Ambulatory Cardiac Monitoring", IEEE Transactions on Biomedical Engineering, vol. 54, No. 5, 2007, pp. 874-882.

Singh et al, "Optimal Selection of Wavelet Basis Function Applied to ECG Signal Denoising", Digital Signal Processing, vol. 16, 2006, pp. 275-287.

Addison, "Wavelet Transforms and the ECG: A Review", Physiological Measurement, vol. 26, 2005, pp. R155-R199.

Popov et al, "Computation of Continuous Wavelet Transform of Discrete Signals With Adapted Mother Functions", Proceedings of SPIE, vol. 7502, 2009, pp. 1-6.

Pinheiro et al, "Stationary Wavelet Transform and Principal Component Analysis Appilcation on Capacitive Electrocardiography", The International Conference on Signals and Electronics Systems, 2010, pp. 37-40.

Sakoe et al, "Dynamic Programming Algorithm Optimization for Spoken Work Recognitino", IEEE Transactions on Acoustics, Speech, and Signal Processing, vol. ASSP-26, No. 1, 1978, pp. 43-49.

Myers et al, "A Comparative Study of Several Dynamic Time-Warping Algorithms for Connected-Word Recognition", The Bell System Technical Journal, vol. 60, No. 7, 1981, pp. 1389-1409.

* cited by examiner

ACTIGRAPHY METHODS AND APPARATUSES

The following relates generally to the medical monitoring arts, actigraphy arts, sleep assessment arts, and related arts.

Actigraphy is a relatively unobtrusive method of monitoring human rest/activity/sleep cycles. The subject being monitored wears a small device which comprises an accelerometer and which is used to measure gross motor activity. Typically worn at the location of the wrist, the actigraphy device is mostly deployed in a wrist-watch-like form factor, which is familiar, and relatively comfortable to the user. Actigraphy is gaining acceptance for ambulatory and home-based sleep assessment, in the healthcare as well as the consumer domain. Actigraphy devices such as the Actiwatch product line (available from Koninklijke Philips N. V., Eindhoven, the Netherlands) are accepted clinical tools for monitoring sleep/wake patterns and to help identify and monitor Circadian Rhythm Disorders, Insomnia, Shift work disorders, and so forth. These devices may be worn on mid-to long-term investigations, typically spanning weeks or months. Actigraphy advantageously provides a time log of activity over the investigation period.

In some situations, body movements cannot be measured using displacement, velocity or acceleration sensors placed on the person's body or on a support system such as a chair or a bed. For example, such a situation may arise for monitoring systems that do not include an actigraphy device on-board or readily incorporated. For example, a Holter monitor (also known as an Ambulatory Electrocardiography device) uses electrocardiography (ECG) to monitor cardiac activity during extended periods of 24 hours or longer. Based on these measurements, cardiologists or other physicians can diagnose the presence of cardiac disorders.

The following discloses a new and improved systems and methods that address the above referenced issues, and others.

In accordance with one aspect, a physiological monitoring device comprises a sensor configured to generate a physiological parameter signal as a function of time for a physiological parameter other than body motion, and an electronic digital signal processing (DSP) device configured to perform operations including: computing a body motion artifact (BMA) signal as a function of time from the physiological parameter signal, and computing an actigraphy signal as a function of time from the BMA signal.

In accordance with another aspect, a physiological monitoring method comprises: receiving a physiological parameter signal as a function of time for a physiological parameter other than body motion; computing a body motion artifact (BMA) signal as a function of time from the physiological parameter signal; and computing an actigraphy signal as a function of time from the BMA signal. The computing operations are suitably performed by an electronic data processing device. In some embodiments, the operation of computing a BMA signal as a function of time from the physiological parameter signal comprises computing a local signal variance signal from the physiological parameter signal, computing a Short-Time Fourier Transform (STFT) signal from the physiological parameter signal, or computing a wavelet transform signal from the physiological parameter signal.

In accordance with another aspect, a non-transitory storage medium stores instructions readable and executable by an electronic data processing device to perform a physiological monitoring method comprising: computing a body motion artifact (BMA) signal as a function of time from a physiological parameter signal as a function of time for a physiological parameter other than body motion; and computing an actigraphy signal as a function of time from the BMA signal.

The invention may take form in various components and arrangements of components, and in various steps and arrangements of steps. The drawings are only for purposes of illustrating the preferred embodiments and are not to be construed as limiting the invention.

FIG. 1 diagrammatically illustrates an ambulatory subject monitoring system including an actigraphy synthesis module as disclosed herein.

FIGS. 4($a$) and 4($b$) illustrate the local signal power computed for two full night recordings.

Figure 5:
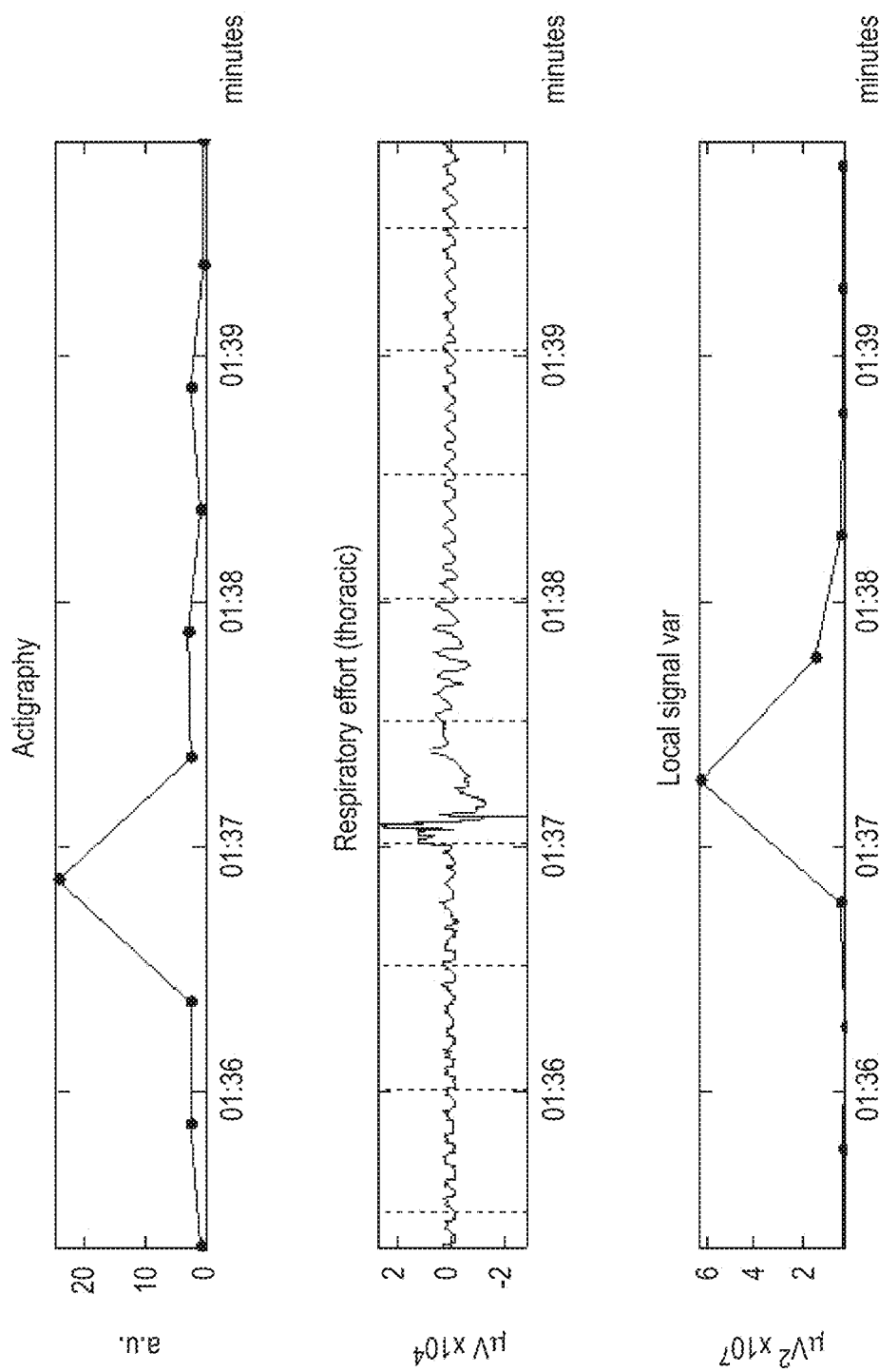

FIG. 5 illustrates a short respiratory effort segment along with simultaneously acquired accelerometer-based actigraphy and the local variance.

Figure 6:
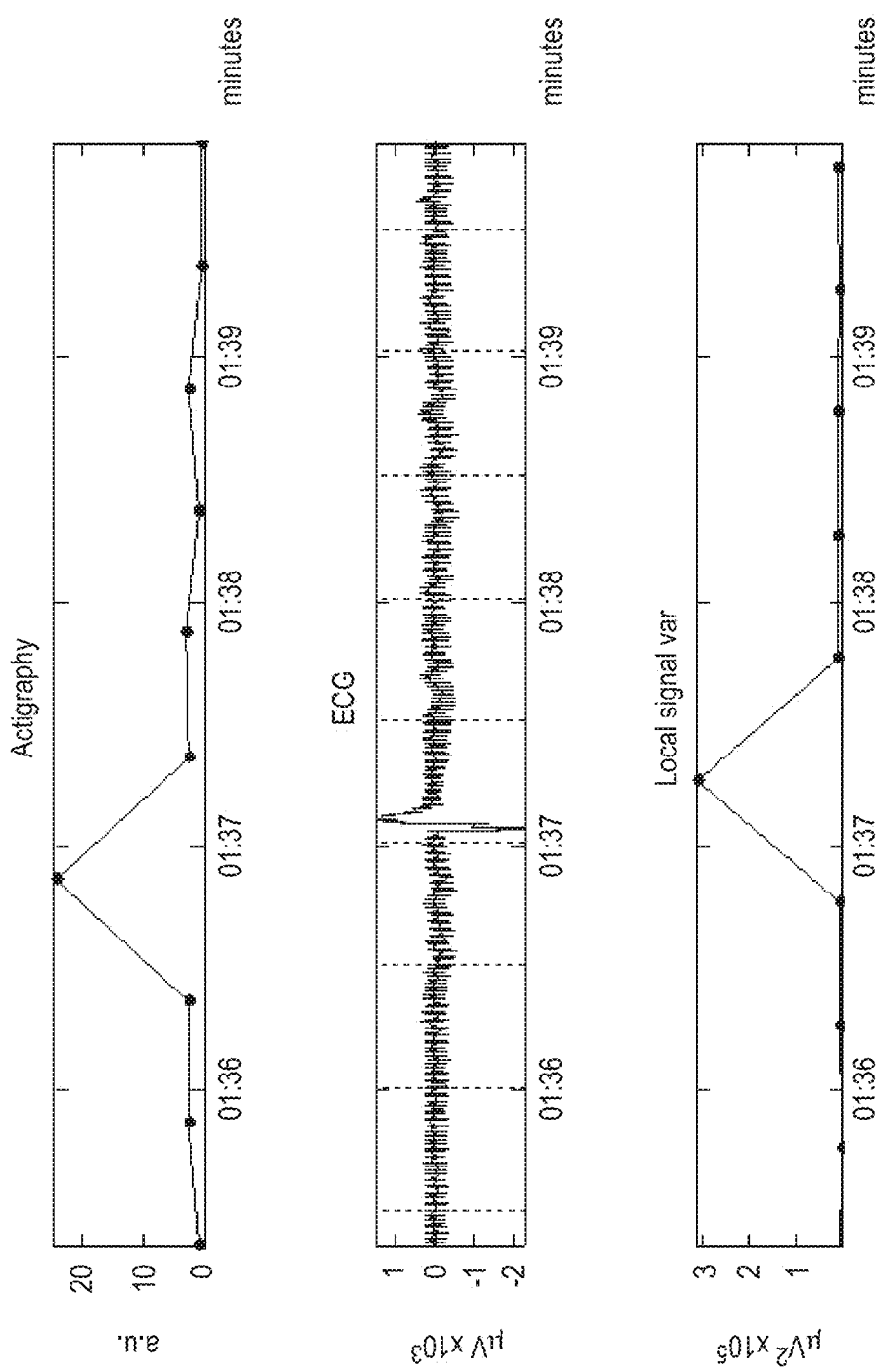

FIG. 6 illustrates a computed local signal variance on an ECG signal.

Figure 7:
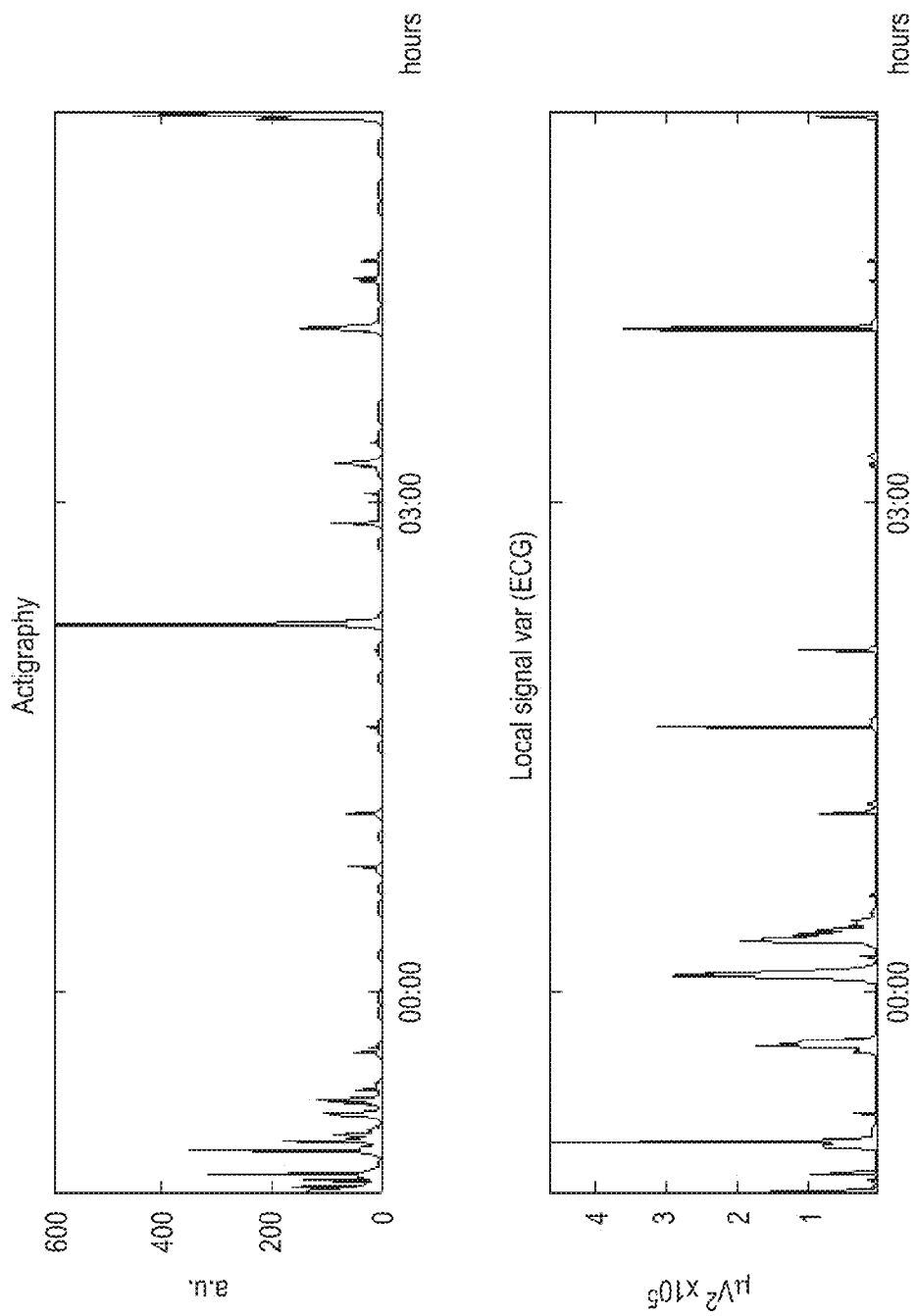

FIG. 7 illustrates a local signal variance on a full night ECG recording.

Figure 8:
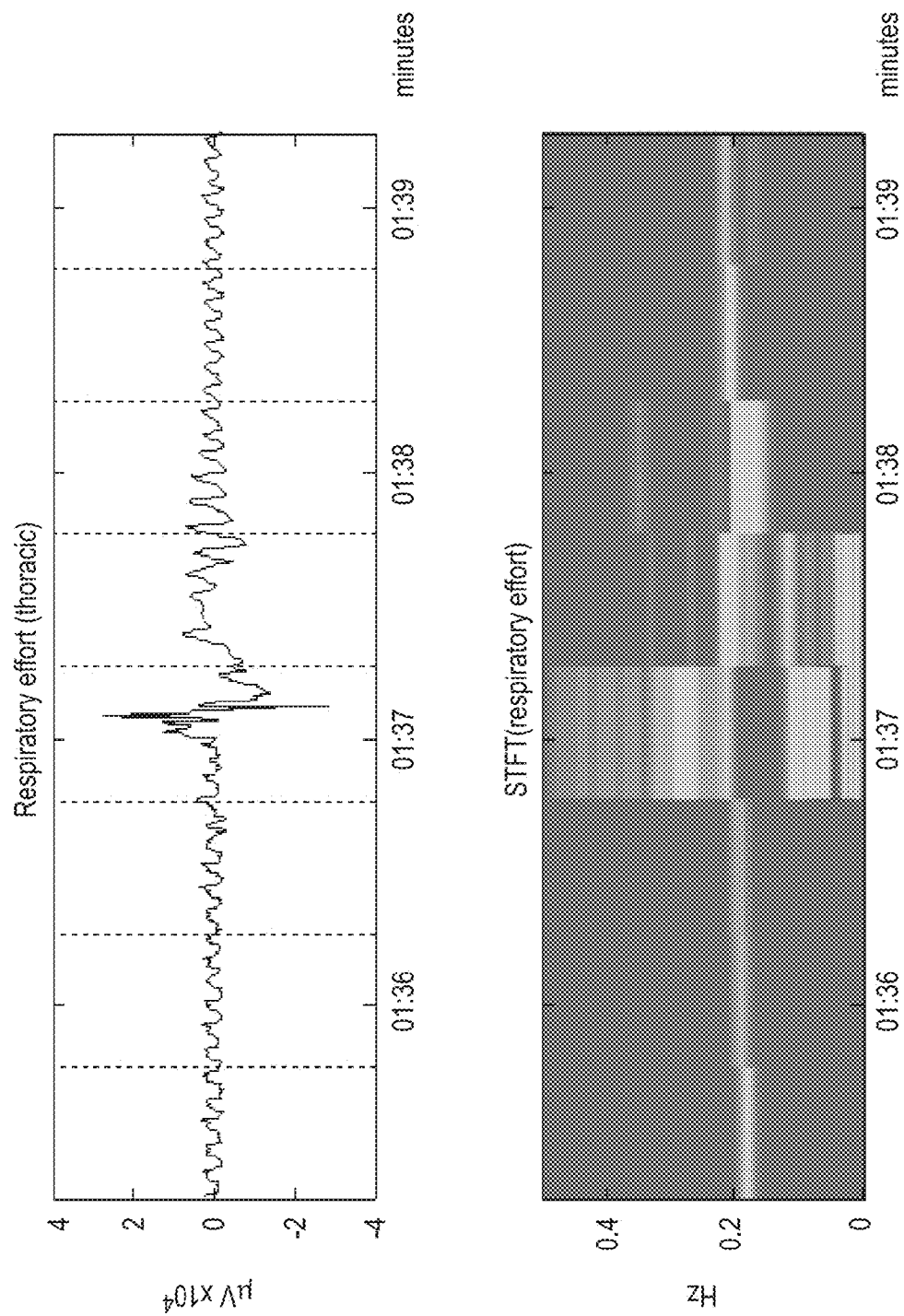

FIG. 8 illustrates a spectrogram representation of a segment of a respiratory effort signal with a Body Movement Artifact (BMA), along with simultaneously acquired accelerometer-based actigraphy.

Figure 9:
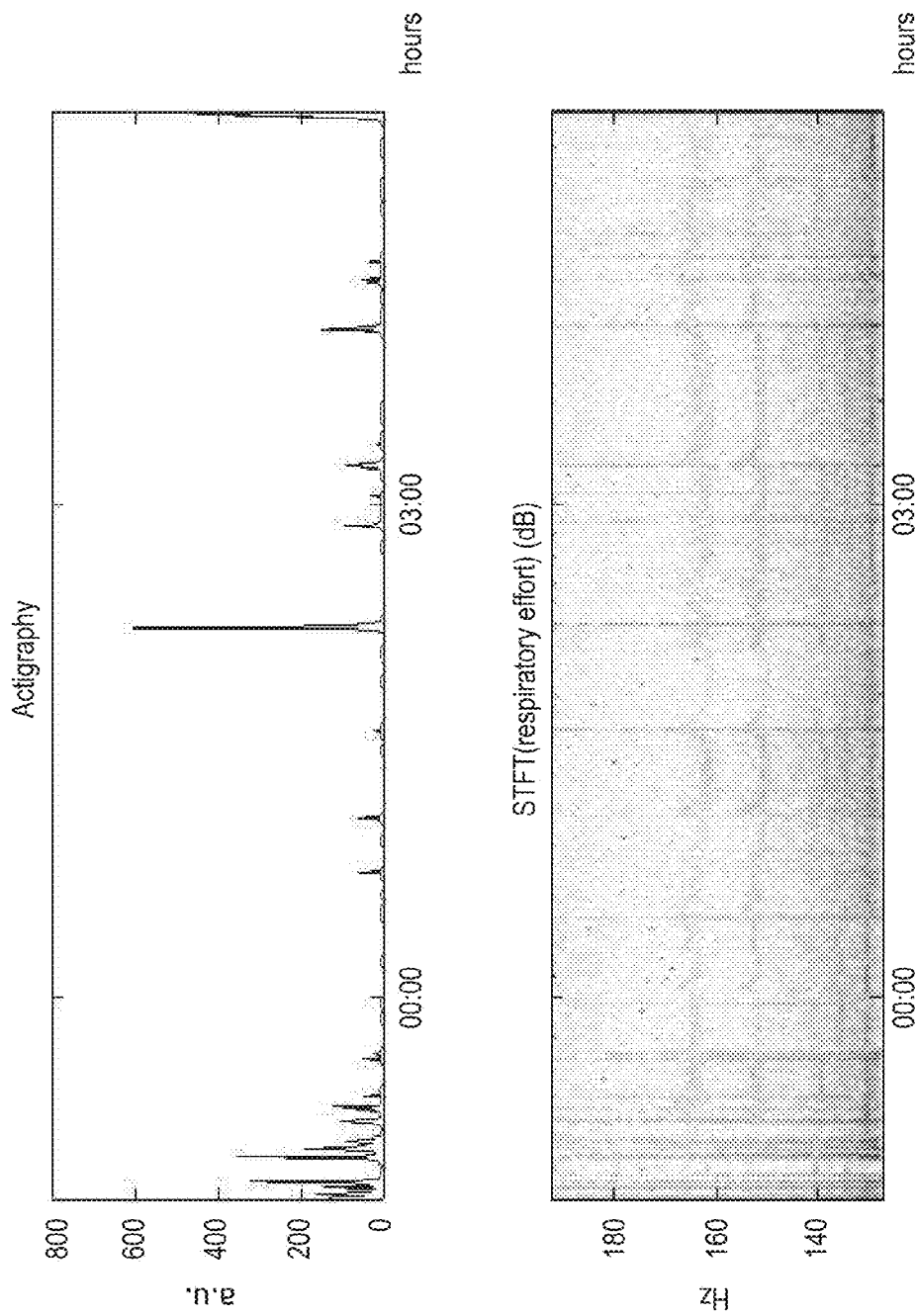

FIG. 9 illustrates a spectrogram of a respiratory effort signal for a full night recording, together with a simultaneously recorded accelerometer-based actigraphy signal.

Figure 10:
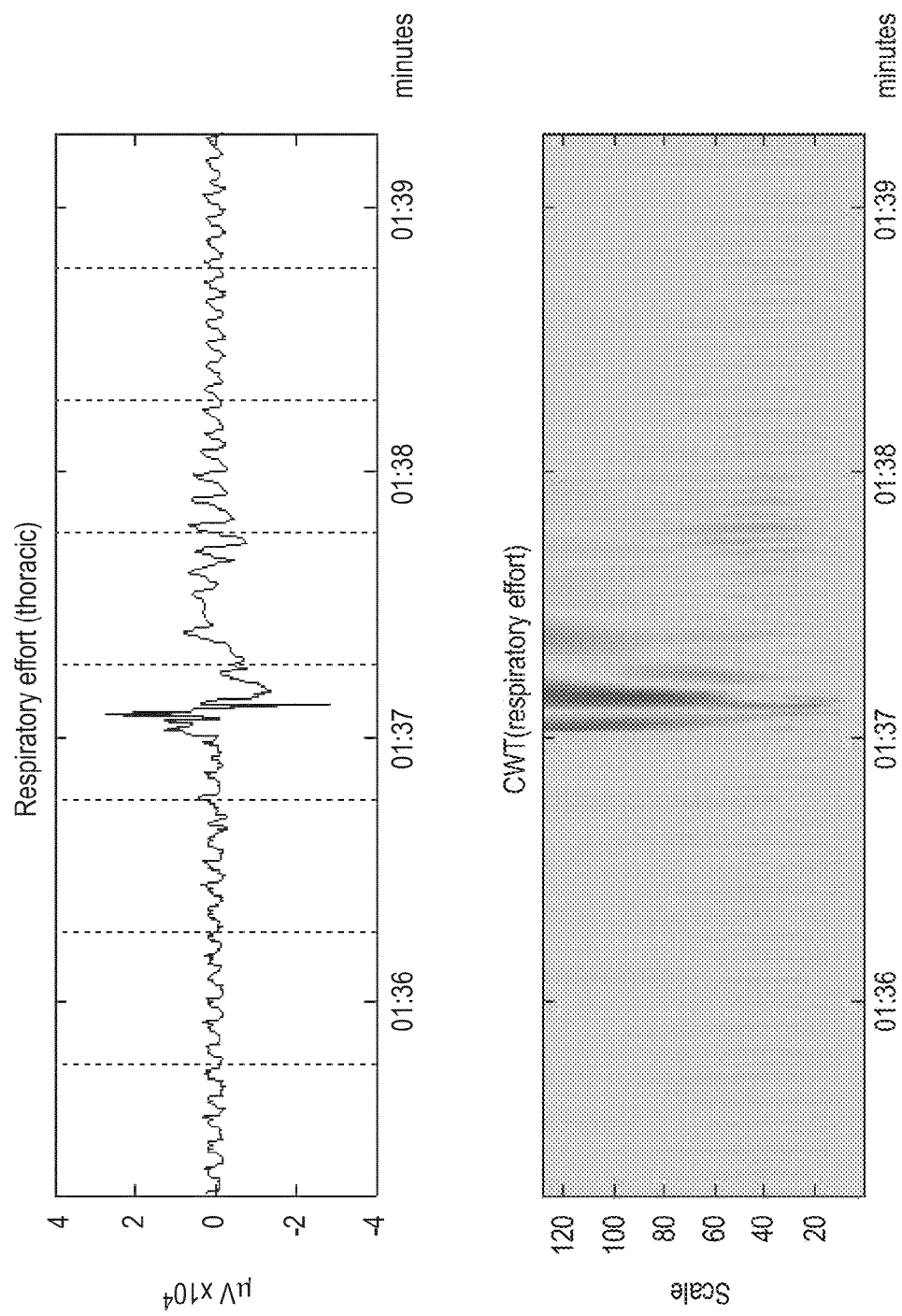

FIG. 10 presents a scalogram illustrating continuous wavelet transform (CWT) values obtained with a db4 wavelet on 128 scales for each sample of a respiratory effort signal segment with a BMA.

Figure 11:
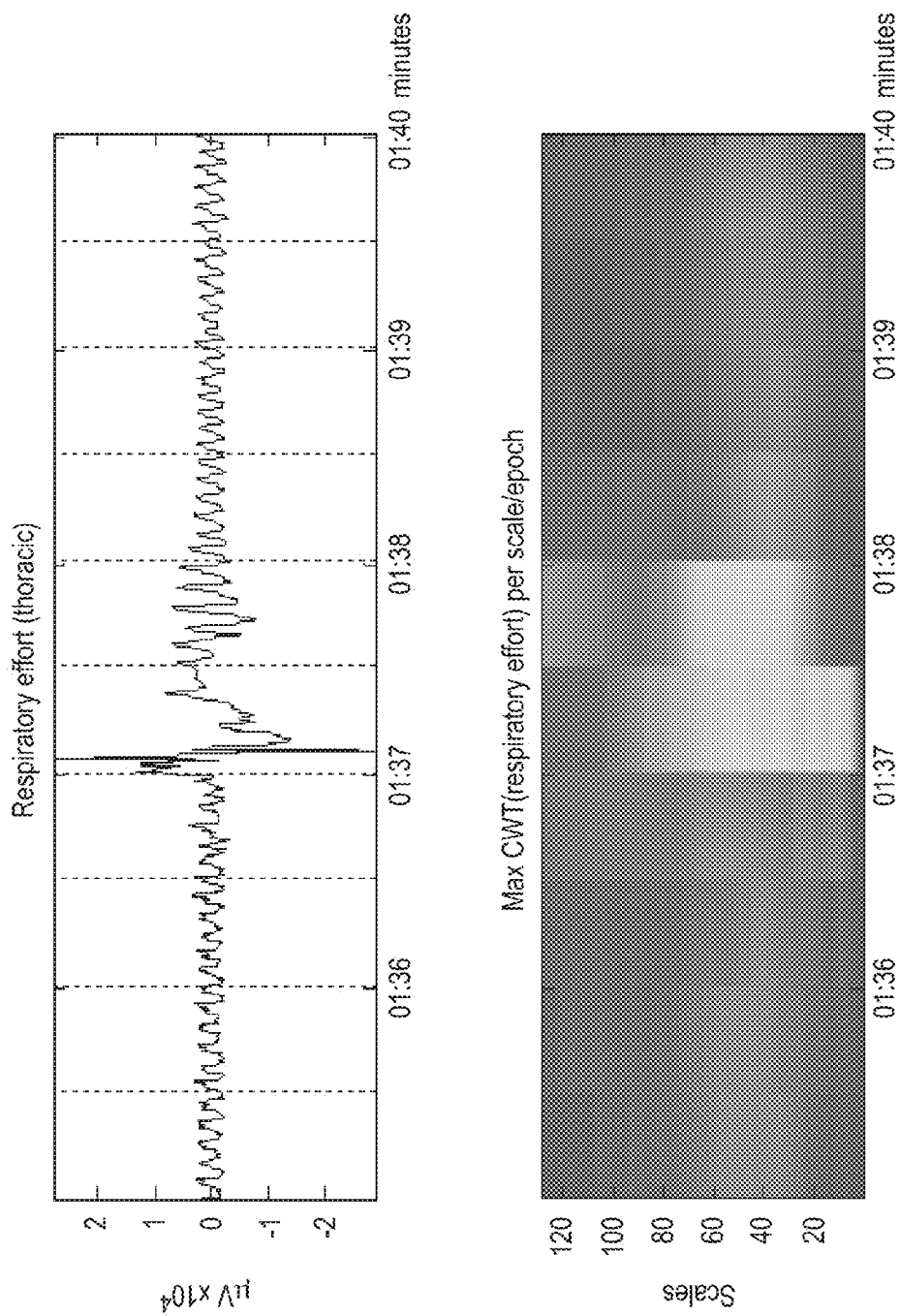

FIG. 11 illustrates the values obtained after taking the maximum CWT value for each scale within the boundaries of each epoch (where each epoch is delineated with dashed vertical lines in the respiratory effort plot).

Figure 12:
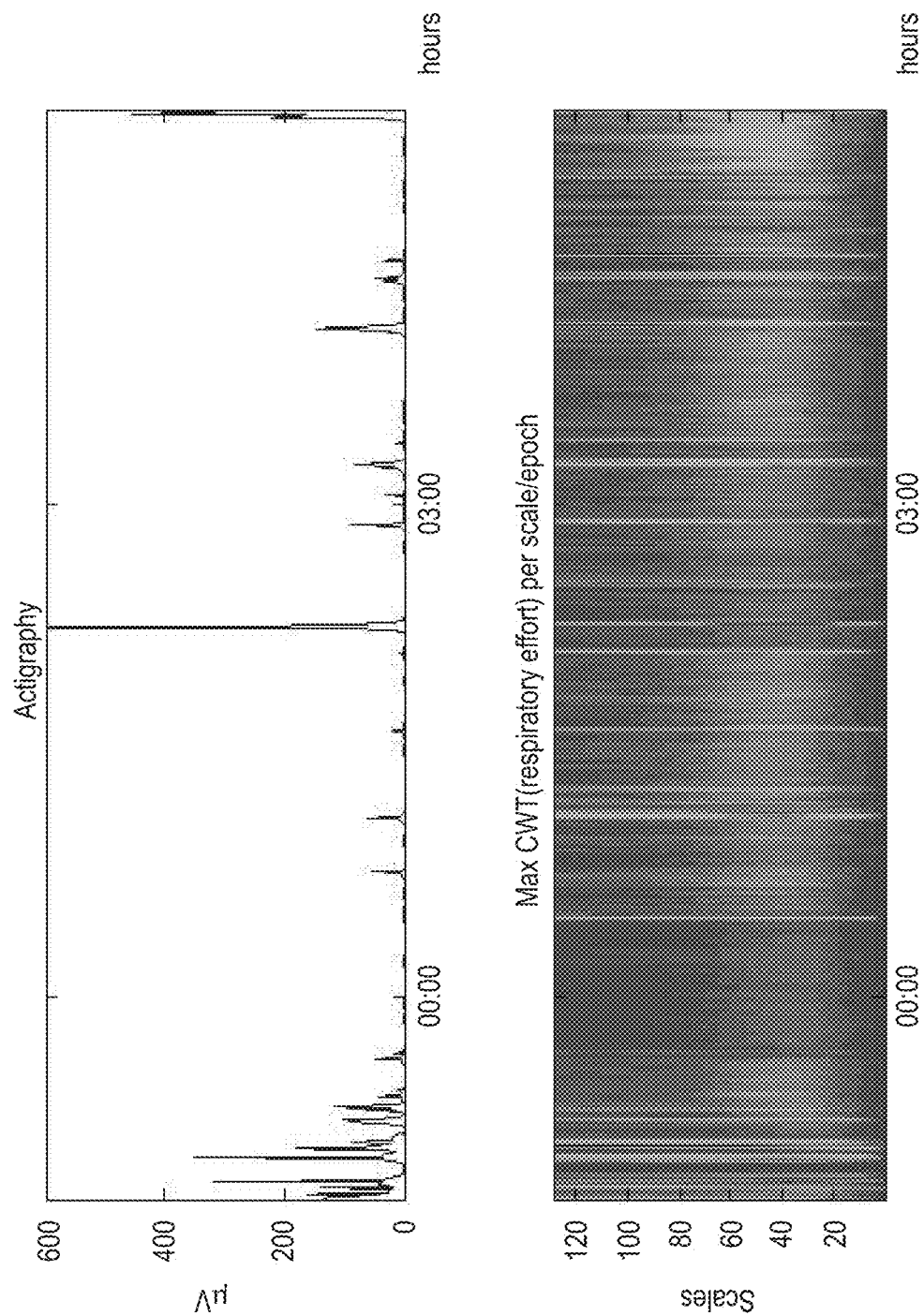

FIG. 12 illustrates CWT-based BMA versus time signal extraction results for a whole-night recording.

Figure 13:
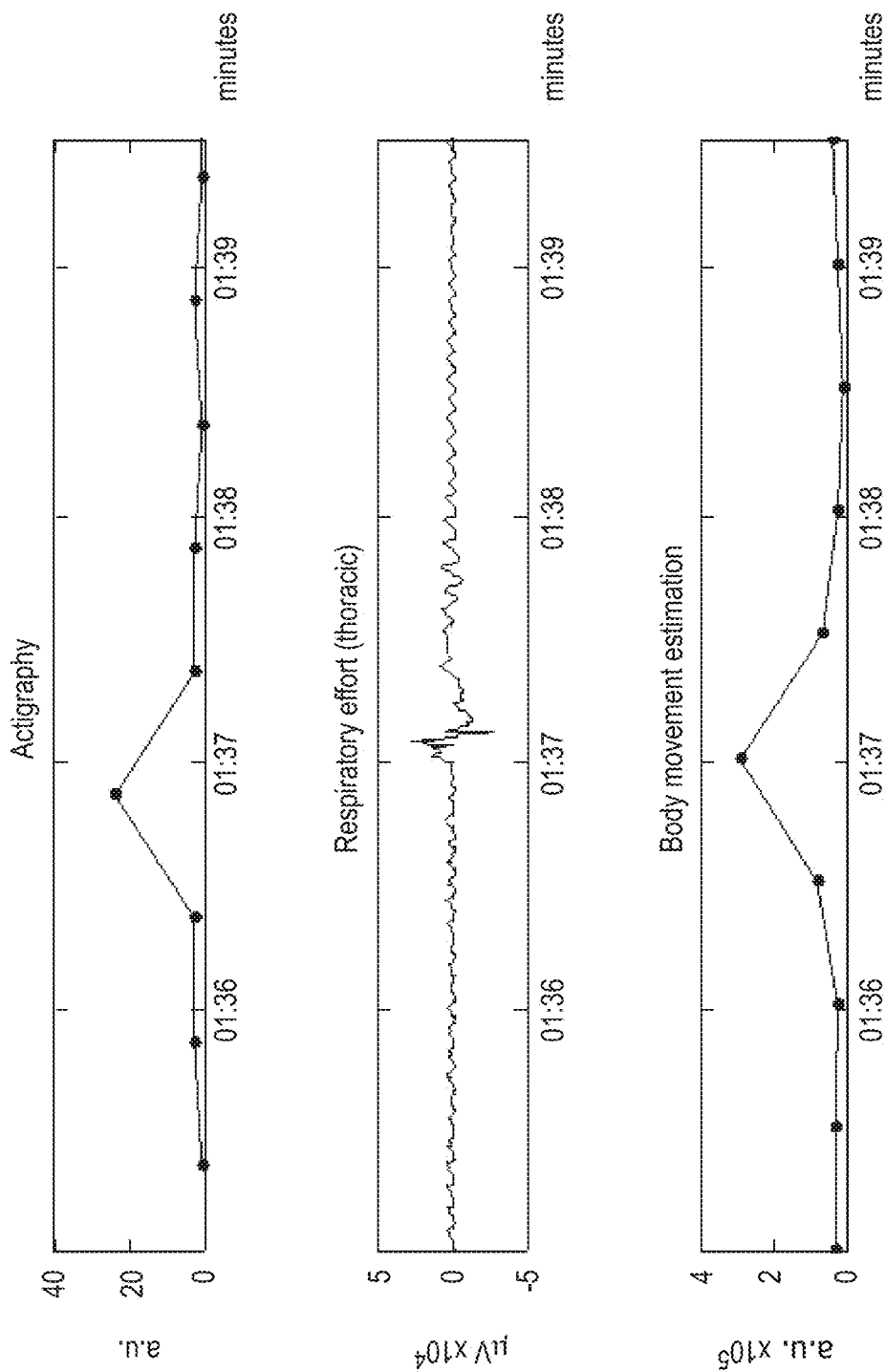

FIG. 13 plots an example of an accelerometer-based actigraphy signal (top plot), respiratory effort signal with a BMA (middle plot) and body movement estimation obtained with the Maximum CWT coefficients for each epoch (bottom plot).

Figure 14:
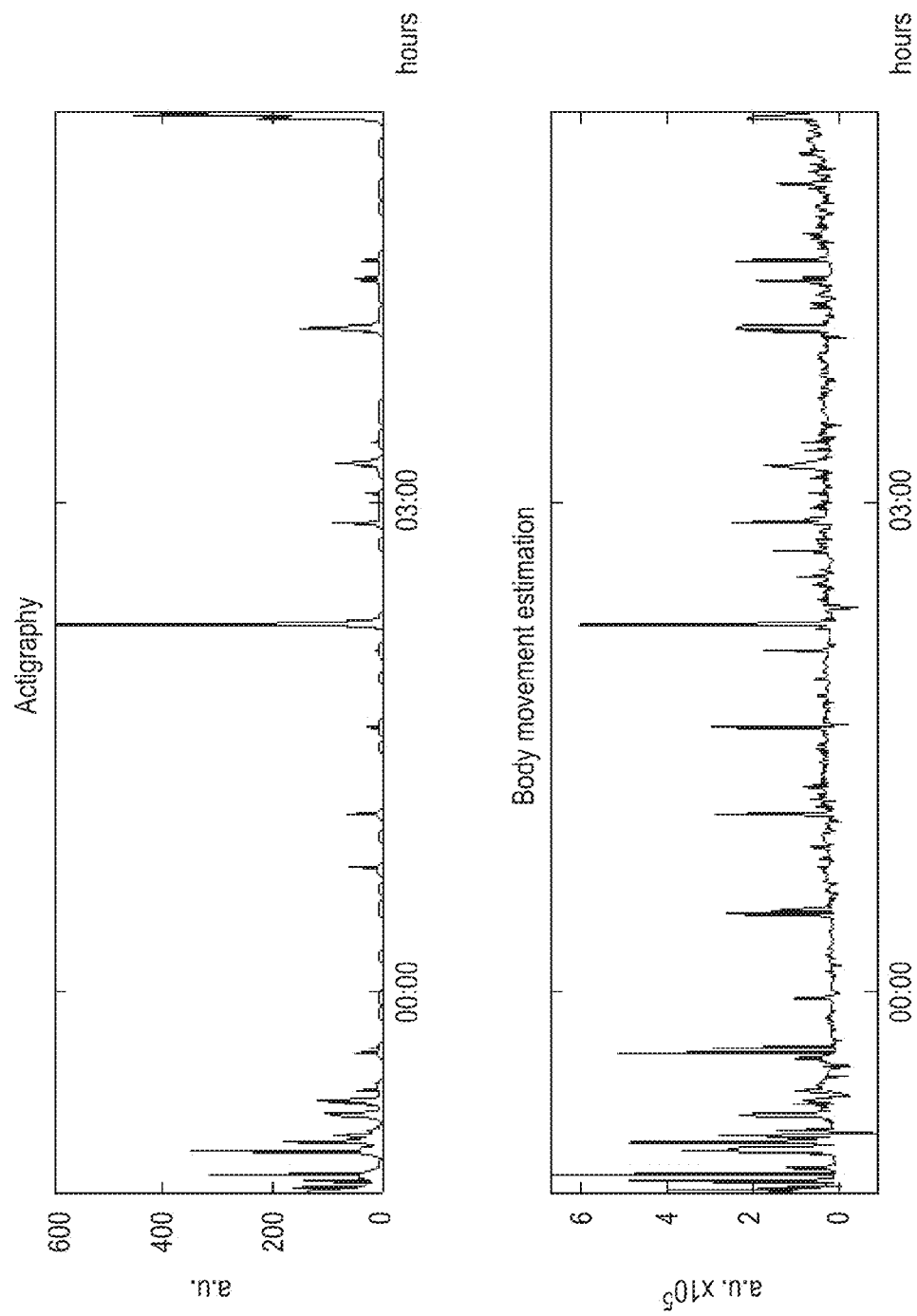

FIG. 14 plots an example of an accelerometer-based actigraphy signal (top plot) and body movement estimation (bottom plot) for a full night recording.

Figure 15:
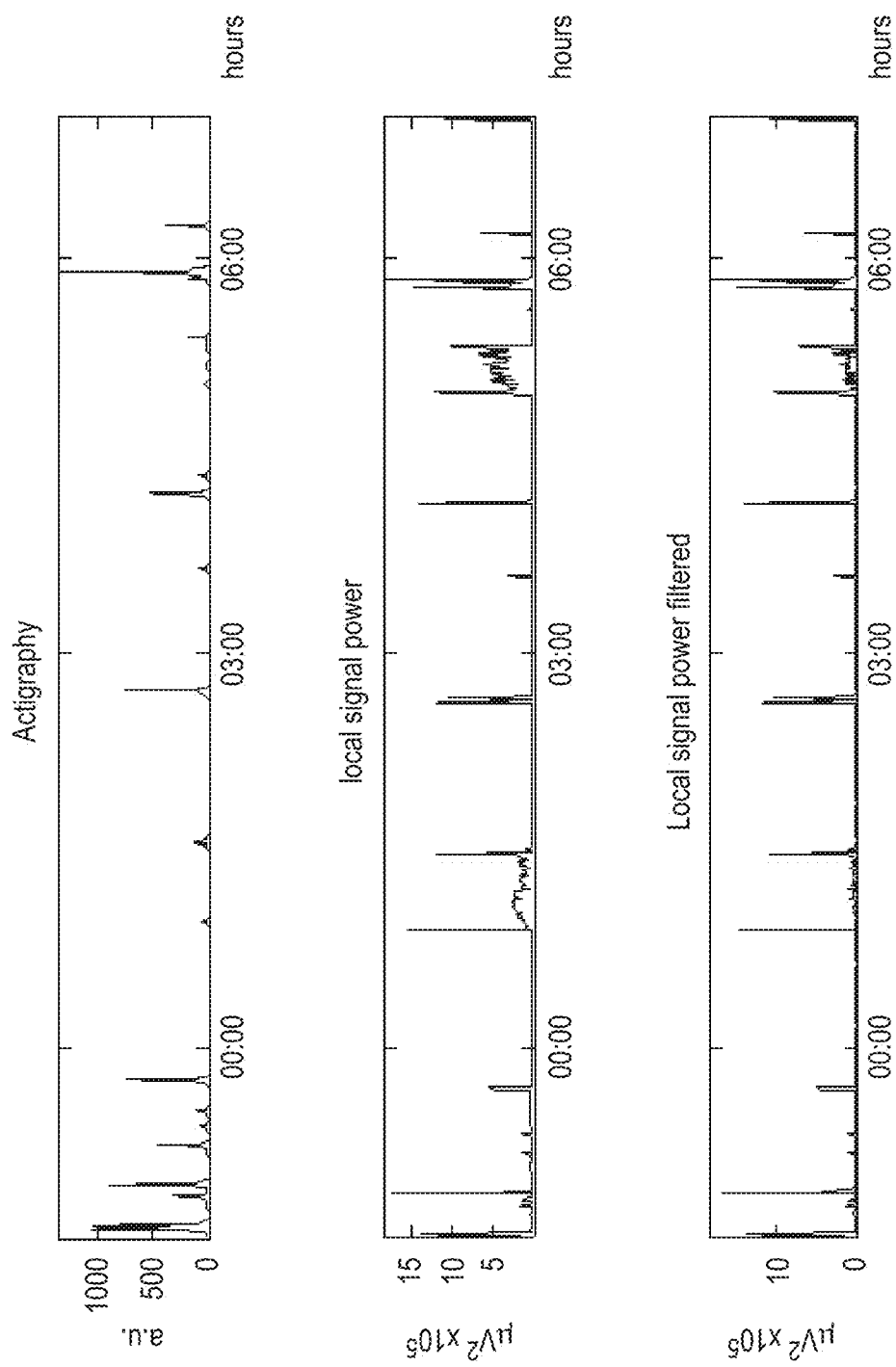

FIG. 15 plots an example of an accelerometer-based actigraphy signal (top plot), the body motion estimation by local signal power from respiratory effort (middle plot) and the body motion estimation signal after filtering by a median removal filter (bottom plot).

Figure 1:
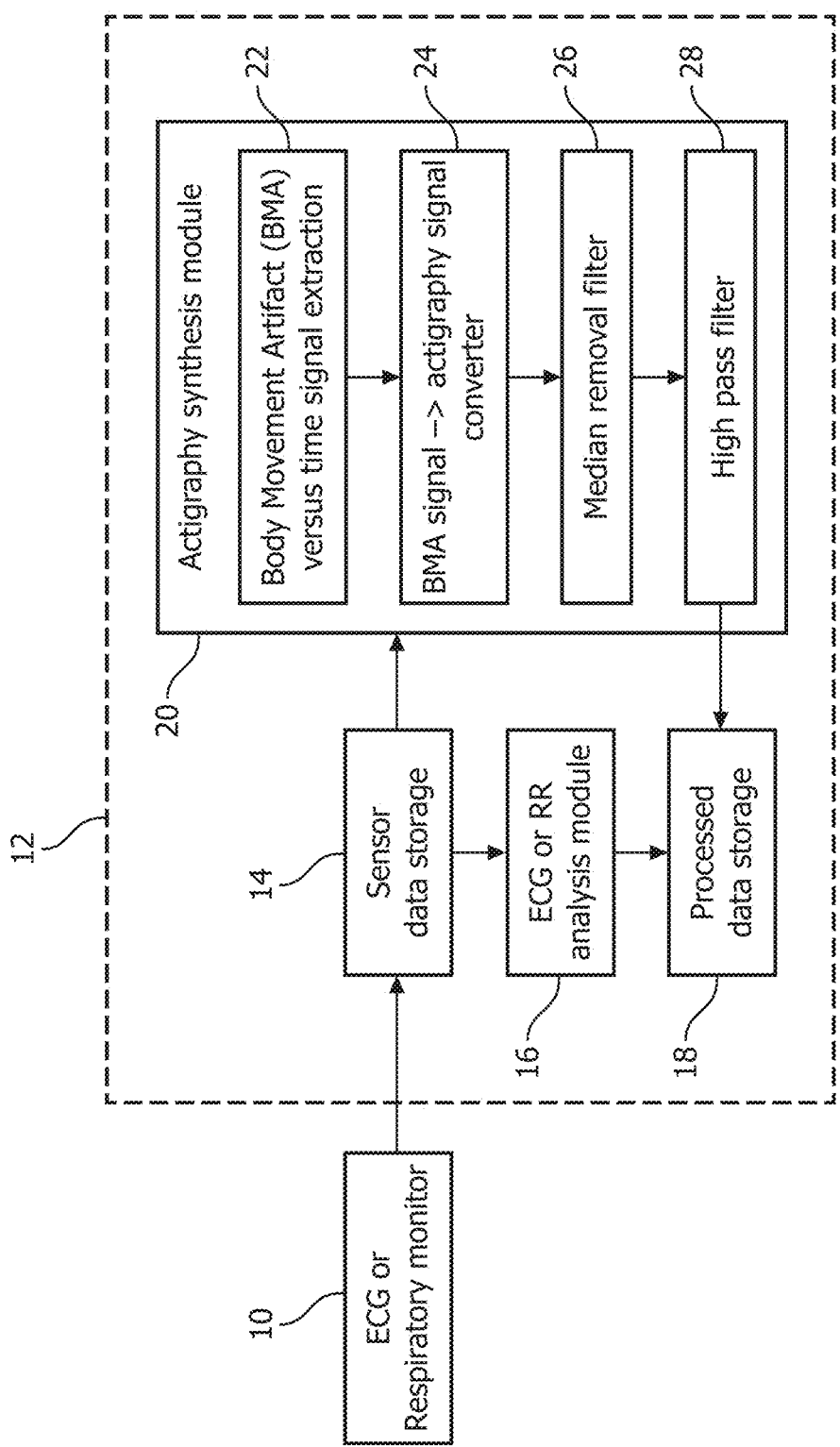

With reference to FIG. 1, an ambulatory subject monitoring system includes one or more physiological sensors 10, each of which sense a physiological parameter other than body movement (displacement, velocity, acceleration). For example, the one or more physiological sensors 10 may include one or more of the following sensors: an ECG sensor; an inductance plethysmography sensor; a photoplethysmography sensor; a ballistocardiography sensor; a nasal pressure sensor; a thoracic impedance sensor; or so forth. Each of the one or more physiological sensors 10 is configured to measure a physiological process other than body movement. For example, the physiological sensors may measure one or more of the following: cardiac activity; thoracic respiratory effort; abdominal respiratory effort; respiratory flow; or so forth. In the illustrative embodiment the one or more physiological sensors 10 include an ECG sensor, a respiratory sensor, or both.

With continuing reference to FIG. 1, the ambulatory subject monitoring system further includes an electronic data processing device 12, for example a microprocessor, microcontroller, or the like, that is programmed to by suitable software or firmware to acquire samples from the one or more physiological sensors 10, store the acquired sensor data in a sensor data storage 14 (for example, a flash memory, magnetic disk or other magnetic memory, or so forth), perform optional post-acquisition sensor data processing 16 (i.e. digital signal processing, "DSP") such as computing ECG lead signals from electrode voltages, computing heart rate (HR) from ECG data, computing respiratory rate (RR) from respiratory sensor data, or so forth, and store the post-acquisition processed data (e.g. ECG signal lead traces, HR, RR, et cetera) in a processed data storage 18 (for example, a flash memory, magnetic disk or other magnetic memory, or so forth; the data storages 14, 18 may optionally comprise a single physical data storage element, e.g. a single flash memory, configured to have logical storage structures for the acquired sensor data and post-acquisition processed data).

The electronic data processing device 12 is further programmed to by the software or firmware to implement an actigraphy synthesis module 20, including performing a Body Movement Artifact (BMA) versus time signal extraction process 22, performing a BMA signal to actigraphy sensor signal process 24 (where the generated actigraphy sensor signal is again a function of time), and performing optional further processing such as illustrative median removal filtering 26, high pass filtering 28, or so forth. The resulting BMA signal is suitably stored in the processed data storage 18.

The ambulatory subject monitoring system of FIG. 1 may optionally include various other features not illustrated in diagrammatic FIG. 1, such as a wired or wireless communication interface (e.g. a USB port, Bluetooth wireless interface, et cetera), an on-board LCD or other display component, buttons or other user interface features to enable a user to perform configuration options such as inputting subject identification, choosing parameters to measure (in embodiments in which the one or more sensors 10 include more than one sensor), choosing post-acquisition processing options, et cetera.

The BMA versus time signal extraction process 22 may use various processing to derive this signal, such as computing the local signal power in the time domain, computing the regularity of the signal in the time domain, computing signal power in the time-frequency domain (for example by means of a Wavelet Transform), computing local signal power in the frequency domain (for example by means of Discrete Fourier Transform), or so forth. The output of the BMA versus time signal extraction process 22 is a BMA signal versus time. In embodiments in which the process 22 employs frequency domain processing (e.g. local signal power), this can be achieved by performing the frequency domain processing over a small time window (also called an "epoch" herein) which is of sufficiently short duration to approximate a signal versus time. Said another way, the time window or epoch affects the temporal resolution of the BMA versus time signal, and should be short enough that the temporal resolution is high, e.g. a few minutes, a few tens of seconds, or better.

In general, body movements can influence measured physiological signals. Such influence can arise as a consequence of mechanical limitations of sensing systems. For example, when measuring an ECG, body movements will cause the skin to deform, changing its capacitance and impedance. ECG electrodes will sense these changes which will result in artifacts corresponding to large amplitude signals on the signal.

As another example, Respiratory Inductive Plethysmography (RIP) is a method for measuring respiratory effort (thoracic or abdominal). A RIP sensor suitably includes elastic wires coated with conductive material, which are sewn on elastic bands that are placed around the ribcage and the abdomen. The cross-sectional area of these body parts expands and contracts due to respiratory excursion, but also due to body movements. The inductance of the conductive elements of the RIP is proportional to the cross-sectional area or the body part they enclose, and hence small and large body movements will both result in artifacts in the measured respiratory effort signal.

Due to the mechanical properties of these sensors, certain properties of the artifacts are closely related to the intensity or amplitude of the body movements. Typically, in the time domain, a higher transitional signal power is observed in the presence of large movements. In the frequency domain, the presence of wide-band noise is observed, with an substantial low-frequency component. Suitable signal processing is employed by the BMA signal→ actigraphy converter process 24 quantifies these artifacts into a measure of body movement.

In the following, some illustrative embodiments of the BMA versus time signal extraction process 22 are described in additional detail.

Figure 2:
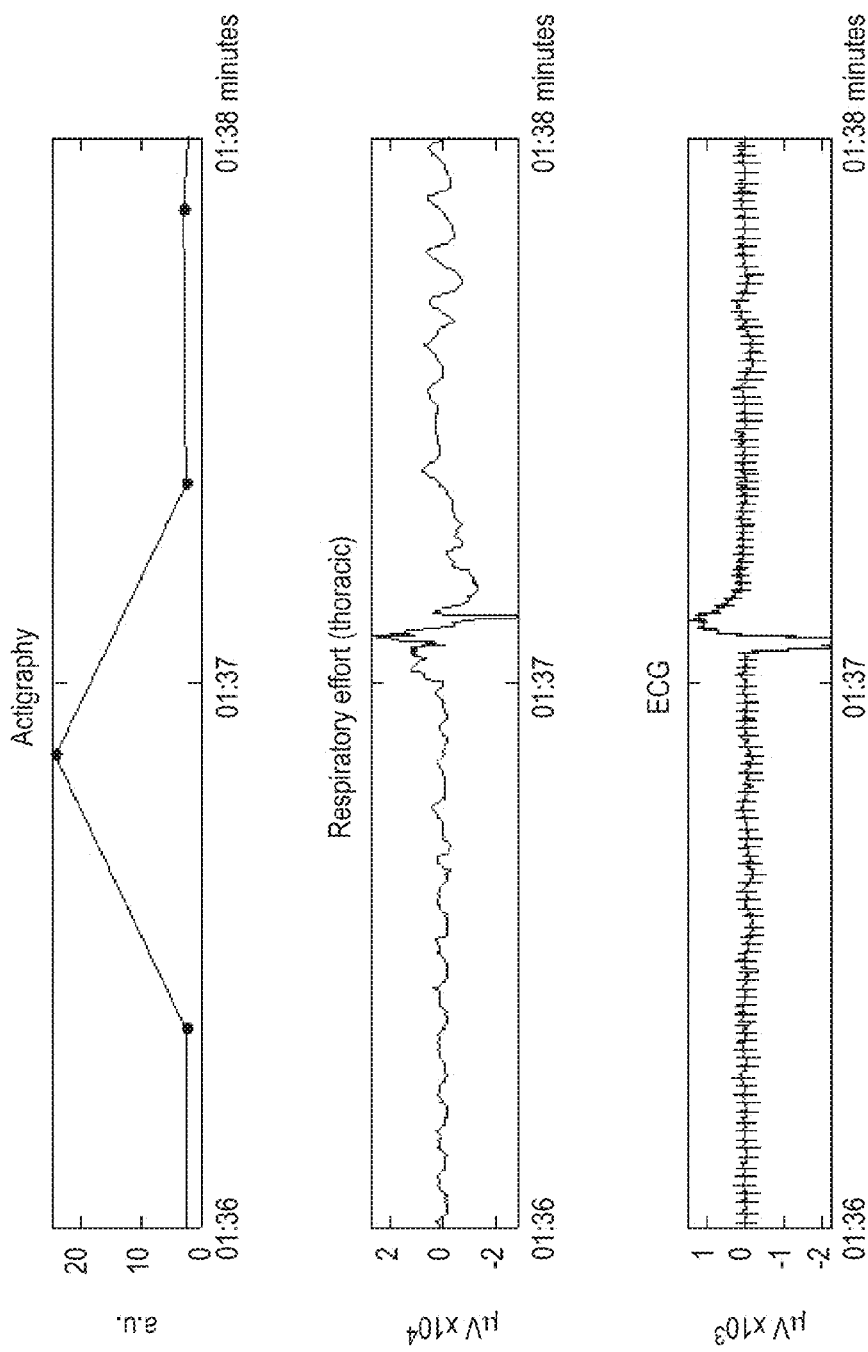
FIG. 2 illustrates an example of a simultaneously recorded actigraphy, respiratory effort (thoracic) and ECG signals, with an artifact.

FIG. 2 illustrates an example of a simultaneously recorded actigraphy, respiratory effort (thoracic) and ECG signals, with an artifact. Note that the signals have different sampling rates. The period of the actigraphy signal is 30 seconds. The peak in the actigraphy signal corresponds to a body movement that took place within a 30-second interval centered around the temporal location of that peak. This body movement produced observable artifacts in the respiratory effort and in the ECG signals as seen in the middle and lower plots, respectively, of FIG. 2.

Body movement artifacts (BMA) in a physiological signal typically have different time and frequency characteristics than the expressions of physiological processes measured by the different sensors 10. As such, these characteristics can be exploited to distinguish artifacts from the physiological signal being measured in process 22, and also to quantify them as a measure of body movements using the processing 24. Some suitable embodiments of such processing are described in the sequel. In general, the actigraphy signal is derived by detecting artifacts in the sensor signal (process 22) and performing transformation processing 24 to generate the actigraphy signal. The following illustrative examples process a single sensor signal, but generalization to multiple sensor signals is straightforward: for example, given a multi-lead ECG signal, from every lead an actigraphy signal is derived, and these signals are combined using suitable data fusion techniques such as addition or averaging of the signals.

In one illustrative example, the process 22 generates the BMA signal versus time by computing local signal power. This approach is based on the observation made herein that body movement artifacts generally increase the local signal power. Intuitively, this can be understood as the body movement introducing additional energy. Furthermore, it is observed herein that the amplitude of these artifacts, and thus, the signal power, is approximately related to the amplitude or intensity of the body movements.

However, signal power is a frequency-domain quantity. Treating the signal power as an actigraphy signal would therefore lose temporal information; that is, while the magnitude of movement could be assessed, its behavior as a function of time is lost.

To overcome this limitation, it is disclosed herein to compute the local signal power over time windows (also called "epochs") of a certain relatively short duration so as to differentiate epochs in which BMAs are present from epochs where they are absent while giving a measure of the amplitude or intensity of the body movement for each epoch. The local power of a signal x on an epoch i is given by:

$$p[i] = \frac{1}{N} \sum_{n=i}^{i+N-1} x^2[n] \qquad (1)$$

where N is the number of samples in each epoch (the window size). By keeping N small, good time resolution is provided. This is at the cost that the signal power p[i] is made less accurate since it is based on only a few samples—but the accuracy is sufficient to provide a reasonably representative actigraphy signal versus time.

Figure 3:
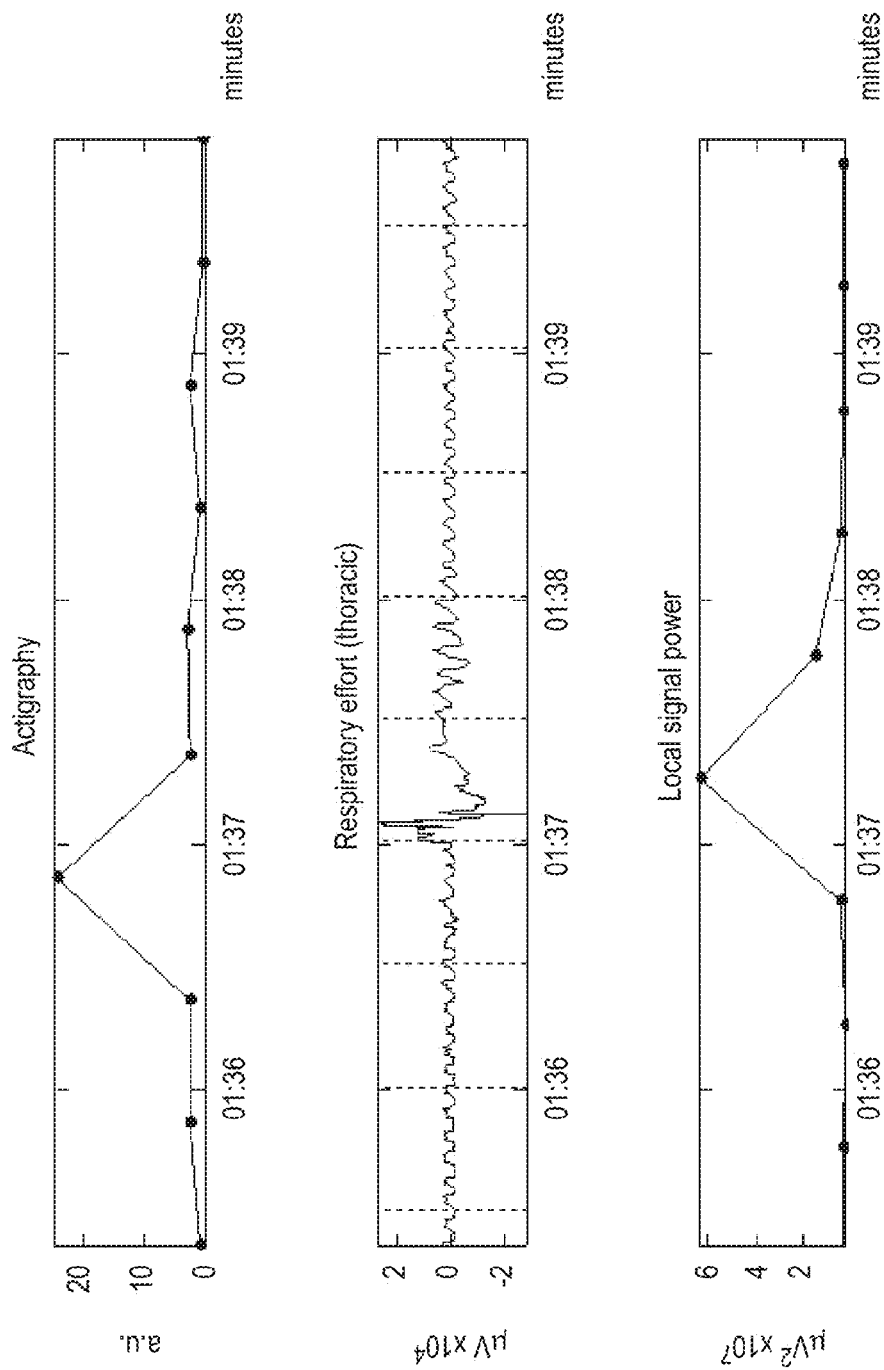
FIG. 3 illustrates an example of the computed local signal power for a segment of a respiratory effort signal.

FIG. 3 illustrates an example of the computed local signal power for a segment of a respiratory effort signal. For reference, FIG. 3 also illustrates simultaneously measured actigraphy measured using an accelerometer-based actigraphy sensor. As it can be seen in FIG. 3, the respiratory effort signal has an artifact shortly after 01:37 minute, caused by a body movement (also detected by the actigraphy signal). The local signal power was computed for 30 second epochs (indicated with dashed vertical bars) from the respiratory effort signal. An increase in local signal power in the fourth and fifth epochs reflect the presence of a BMA.

Figure 4A:
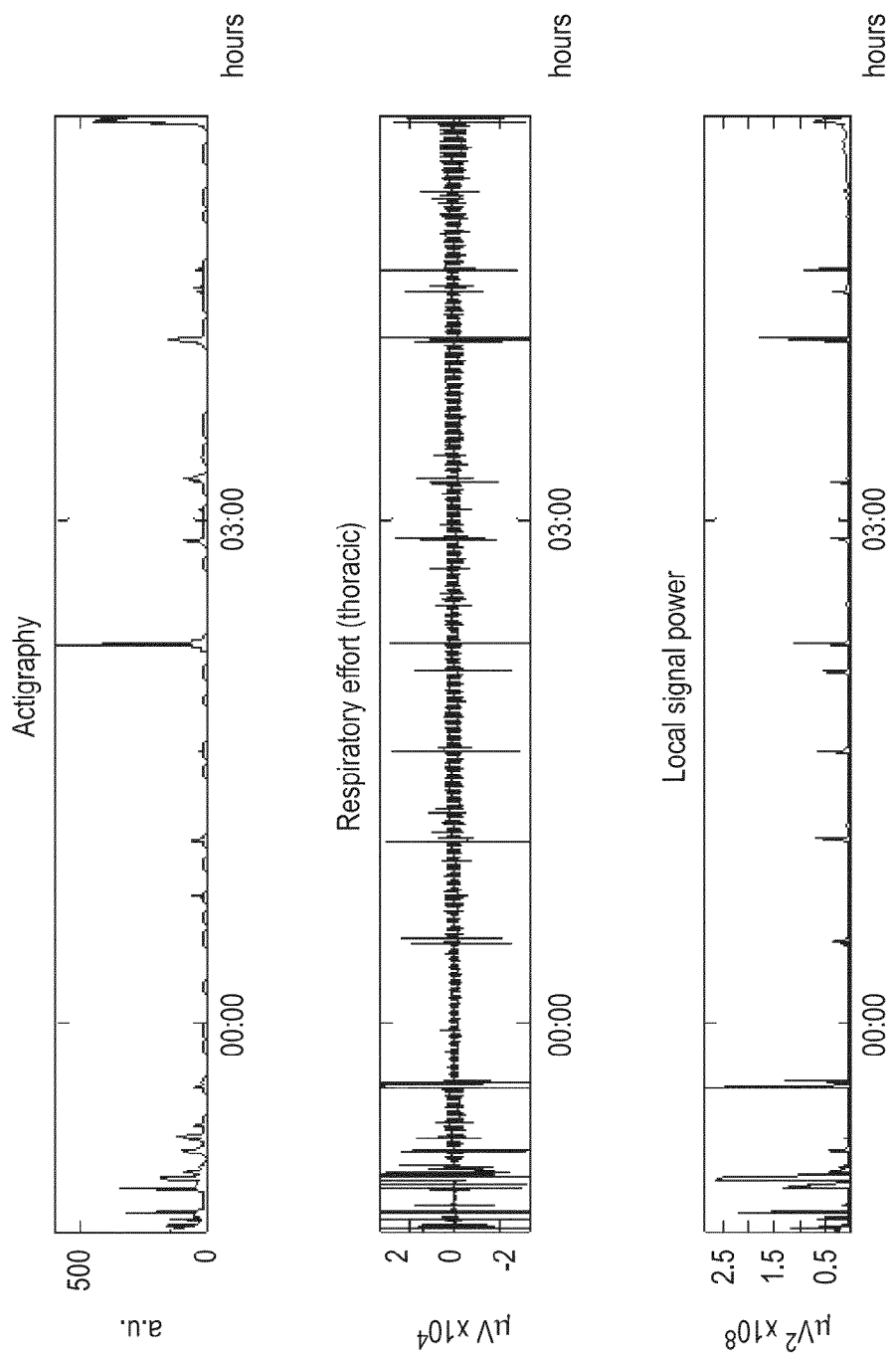
Figure 4B:
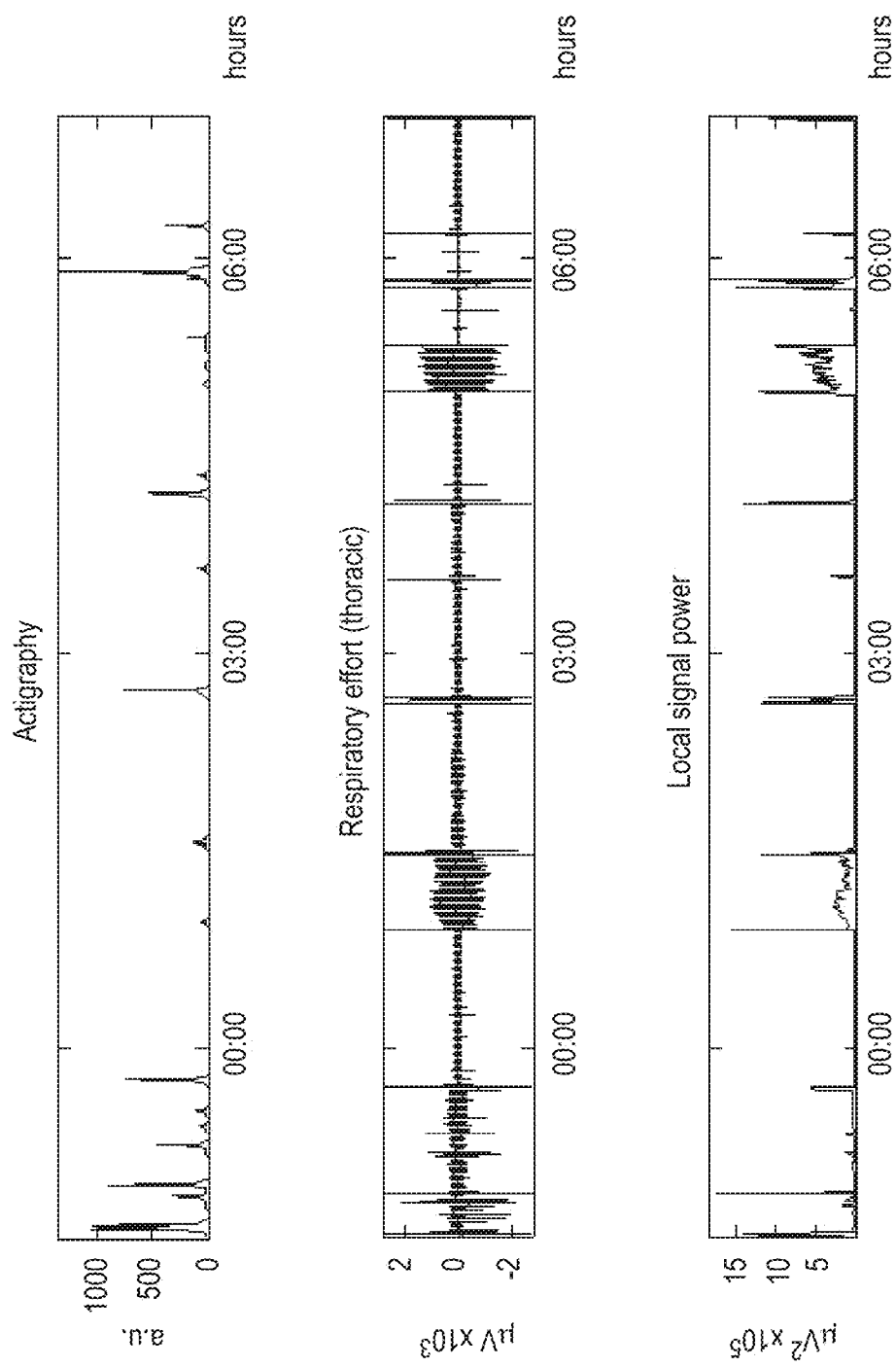

FIGS. 4(a) and 4(b) illustrate the local signal power computed for two full night recordings. In the recording shown in FIG. 4(a), the local signal power correlates well with a simultaneously recorded actigraphy, with peaks on the same time instances. Although the amplitude of the peaks is somewhat different, it is clear that whenever there is a peak of actigraphy, the local signal power also increases.

With reference to FIG. 4(b), a drawback of this technique is illustrated: whenever the local signal power changes not due to body movements, but rather, due to changes in the sensing conditions (such as when the position of a subject lying in bed changes, and the subject lies for some minutes on top of an ECG electrode, or when the respiratory plethysmography belt stretches due to that position), the local signal power might reflect also that situation. This is visible in FIG. 4(b): during several periods during the night (most notably between around 1:00 and 2:00 and then around 5:00) the amplitude of the respiratory effort is larger than in the rest of the recording. Since this follows and precedes significant BMAs, it is likely to have been caused by a change in the lying position. This is reflected in the local signal power as two "plateaus" which do not correspond to artifacts but rather to this change in the amplitude of the signal. In some embodiments, this problem may be overcome by the use of different BMA estimation techniques, or by means of post-processing such as the filtering operations 26, 28.

In another illustrative embodiment, the BMA versus time signal extraction process 22 employs local signal variance processing. This approach is based on the observation made herein that in the presence of BMAs, the variance of the signal changes. Within epochs shorter than a few minutes, most physiological signals vary between reasonably stable minima and maxima. In the presence of BMAs, however, the signal varies beyond these boundaries, increasing the local signal variance significantly. The variance of a signal x on an epoch i is given by:

$$v[i] = \frac{1}{N-1} \sum_{n=i}^{i+N-1} (x[n] - \bar{x}[i])^2 \qquad (2)$$

$$\bar{x}[i] = \frac{1}{N} \sum_{n=i}^{i+N-1} x[n]$$

where N is the number of samples in an epoch.

Note that for piece-wise stationary signals the local signal variance is the same (apart a scaling factor $$\frac{N-1}{N})$$

as the local signal power described earlier.

With reference to FIG. 5, a short respiratory effort segment is illustrated along with simultaneously acquired accelerometer-based actigraphy and the local variance computed using Expression (2). In the case of the short respiratory effort segment illustrated in FIG. 5, the resulting local signal variance is approximately the same as the local signal power computed and illustrated in FIG. 3.

With reference to FIGS. 6 and 7, these techniques can be used on other physiological measurements besides respiratory signals. FIG. 6 illustrates the computed local signal variance on an ECG signal, while FIG. 7 illustrates the local signal variance on a full night ECG recording.

In another illustrative embodiment, the BMA versus time signal extraction process 22 employs discrete Short-Time Fourier Transform (STFT) processing. This approach is based on the observation that the frequency response of a segment of a signal with a BMA is different than of a segment without such artifacts. Computing the Discrete Fourier Transform (DFT) on each of these segments allows a differentiation between the two types of segments. Furthermore, the Fourier coefficients obtained after this transformation also relate to the power of the signal (more precisely to the power of the signal for each frequency). For that reason, they can be used to characterize (e.g. the amplitude) of the body movements. The use of a Short-Time DFT (e.g., computed over an epoch of duration of a few minutes or less, and in some illustrative embodiments of 1 minute or less, advantageously provides the desired time resolution to generate the BMA versus time signal with suitably fine temporal resolution.

The Short-time Fourier Transform (STFT) can be obtained by computing the DFT of the signal for each epoch according to:

$$X[i, \omega] = \sum_{n=i}^{i+N-1} x[n]W[n-i]e^{-j\omega n} \quad (3)$$

where W is a window function which is zero-valued outside of the chosen epoch. A Hamming function, i.e.

$$W[n] = 0.54 - 0.46 \cos\left(2\pi\frac{n}{N}\right),$$

$0 \leq n \leq N$, or otherwise-shaped window may used to reduce spectral leakage when calculating the DFT. Taking the squared magnitude of the DFT, the spectral density of the signal is obtained for that epoch:

$$S[i,\omega] = |X[i,\omega]|^2 \quad (4)$$

With reference to FIG. 8, a spectrogram representation of a segment of a respiratory effort signal with a BMA is illustrated, along with simultaneously acquired accelerometer-based actigraphy. The spectrogram was computed with DFT using a Hamming window of 60 seconds, with overlaps of 30 seconds. The average breathing frequency on the first 3 epochs is clearly visible (with a peak around 0.2 Hz, or 12 breaths per minute). The BMA in epoch 4 and 5 significantly change the power spectral density (PSD) for those epochs, with a strong low frequency component. In this example, before computing the STFT, the DC component was removed from the signal by mean subtraction.

FIG. 9 illustrates the spectrogram of a respiratory effort signal for a full night recording, together with a simultaneously recorded accelerometer-based actigraphy signal. More particularly, FIG. 9 plots the log-spectrogram representation of the respiratory effort signal for a full-night recording (Hamming window of 60 seconds, 30-second overlap). Peaks of activity lead to wide-band increases of spectral power. This shows that the STFT coefficients can be used for detecting and quantizing BMAs.

Although the STFT can detect and quantize BMAs, it has certain performance limitations. The power of each frequency is obtained with a sinusoidal base function, whereas neither the artifacts nor the underlying physiological signals have such a shape. The STFT also has limited resolution, as the width of the epochs (or the windowing function) implicitly determines the frequency resolution. A wider window allows for a better frequency resolution but a poorer time resolution and vice versa.

In another illustrative embodiment, the BMA versus time signal extraction process 22 employs wavelet transform processing. Wavelets have been used as a multi-resolution analysis tool for ECG (see Addison, "Wavelet transforms and the ECG: a review", Physiological measurement, vol. 26, 2005) and for noise and artifact reduction in ECG signals (see Singh et al., "Optimal selection of wavelet basis function applied to ECG signal de-noising", Digital Signal Processing, vol. 16, pp. 275-287, 2006). The continuous wavelet transform of a (continuous) signal x(t) is given by:

$$W_\psi(a, b) = \langle x(t), \psi_{a,b}(t) \rangle = \frac{1}{\sqrt{a}} \int_{-\infty}^{\infty} x(t)\psi^*\left(\frac{t-b}{a}\right) dt \quad (5)$$

where a is a scale factor, b is a translation factor, and $\psi^*(t)$ is the complex conjugate of the mother (wavelet) function. When the mother function can be evaluated at different scales, for different translations, at discrete points, then the continuous wavelet transform (CWT) of a discrete signal is given by:

$$W_\psi[a, i] = \frac{1}{\sqrt{a}} \sum_{n=0}^{N-1} s[n]\psi^*\left[\frac{n-m}{a}\right] \quad (6)$$

where N is the the number of samples in the signal (or window of interest) and m is an integer time translation, $m \in \mathbb{Z}$. See Popov et al., "Computation of continuous wavelet transform of discrete signals with adapted mother functions", Proc. of SPIE, vol. 7502, 2009.

A widely used family of wavelet functions is the so-called "Daubechies" family (db), which has been applied in noise- and artifact-reduction problems such as 4 coefficient-db (see Pinheiro et al., "Stationary wavelet transform and principal component analysis application on capacitive electrocardiography", International Conference on Signals and Electronic Systems (ICSES) 2010, pp. 37-40, 2010) and 8 coefficient-db (see Singh et al., "Optimal selection of wavelet basis function applied to ECG signal de-noising", Digital Signal Processing, vol. 16, pp. 275-287, 2006).

FIG. 10 illustrates a so-called "scalogram" which illustrates the CWT values obtained with a db4 wavelet on 128 scales for each sample of a respiratory effort signal segment with a BMA. It is clear that the artifact causes a mid- to high-scale CWT response. The BMA leads to higher CWT values, especially in mid- and high-scales.

With reference to FIG. 11, since the CWT is computed for each sample in the original signal and characterization of the BMA over an entire epoch is of interest, statistics can be used to obtain one or a few values per scale, per epoch. FIG. 11 illustrates the values obtained after taking the maximum CWT value for each scale within the boundaries of each epoch (where each epoch is delineated with dashed vertical lines in the respiratory effort plot). FIG. 11 clearly shows higher values over the mid-high-scales in the epochs with the BMA.

FIG. 12 illustrates CWT-based BMA versus time signal extraction results for a whole-night recording. The accelerometer-based actigraphy signal is again plotted for reference. As it can be clearly seen, instances that correspond to a peak in the actigraphy signal lead to an increase in the CWT coefficients, especially for mid- and high-scales.

Other approaches for performing the processing 22 are contemplated, such as approaches that exploit signal regularity to quantify artifacts in the signal. An example of such a technique is Dynamic Time Warping [5, 6]. See Sakoe et al., "Dynamic programming algorithm optimization for spoken word recognition", IEEE Transactions on Acoustics, Speech and Signal Processing, 26(1) pp. 43-49, 1978, ISSN: 0096-3518; Myers et al., "A comparative study of several dynamic time-warping algorithms for connected word recognition", The Bell System Technical Journal, 60(7):1389-1409, September 1981.

With returning reference to FIG. 1, after the processing 22 generates the Body Movement Artifact (BMA) versus time signal, the processing 24 processes the BMA-versus-time signal to generate an actigraphy signal versus time. In the case of local signal variance, local signal power or other one-dimensional measure of BMAs, a body movement estimate (BME) can be obtained by suitably scaling and translating that signal according to:

$$e[i] = a \cdot x[i] + b \quad (7)$$

where x is a signal resulting from the quantification of BMAs for each epoch i, and a and b are the scaling and translation factors, respectively. These factors can be obtained, for instance, by linear regression minimization of a given criteria in respect to a reference measure of body movements (e.g. obtained by simultaneous recording of accelerometer-based actigraphy).

In the case of M-dimensional quantifications of BMA (with M>1), a similar procedure can be used:

$$e[i]=a \cdot x[i]+b \qquad (8)$$

where in this case x[i] is an M×1 signal representing the quantification of BMAs for an interval starting at i, a is a 1×M scaling vector, and b is a translation factor or offset. Parameters a and b can be estimated by multivariate linear regression, minimizing a certain criteria in respect to a reference measure of body movements.

As an example, consider the 'Max CWT per epoch' measure, which can be used to obtain scale values for each epoch, with these scale values (especially for medium and higher scales) having a higher value in the presence of BMAs. Using a set of coefficients obtained after linear regression between the maximum CWT coefficients for a set of full night recordings, and a reference accelerometer-based actigraphy signal, the body movement estimates illustrated in FIG. 13 and FIG. 14 are obtained. FIG. 13 plots the accelerometer-based actigraphy signal (top plot), the respiratory effort signal with a BMA (middle plot) and body movement estimation obtained with the Maximum CWT coefficients for each epoch (bottom plot). FIG. 14 plots the accelerometer-based actigraphy signal (top plot) and the body movement estimation (bottom plot) for a full night recording.

Apart from some low-amplitude noise, the BME is seen in these illustrative examples to correlate well with the reference accelerometer-based actigraphy signal, not only in terms of the temporal location of activity peaks, but also in terms of their amplitude which indicates the intensity and duration of body movements.

In an alternative approach for the processing 24, non-linear regressions can be used in order to estimate body movements. This is expected to be especially suitable in the multivariate case, where an M-dimensional space (M>1) is used to quantify the artifacts and where the relations between the dimensions of this space are non-linear (e.g. if one dimension exhibits an exponential variation with the intensity of the artifact—and therefore the body movement). As another contemplated alternative, one can directly classify the quantified artifacts in categorical classes which describe, qualitatively, the type of body movements. In this case, a conventional classifier can be used for that purpose.

With returning reference to FIG. 1, the actigraphy versus time signal generated by the processing 24 is optionally post-processed, for example by the illustrative filters 26, 28. Such post-processing can improve the body movement estimates. A filter can be used, for an example, to reduce the negative impact of the local signal power variations due to the mechanical constraints of the sensors used. Take for instance the local signal power estimated from the respiratory effort signal illustrated in FIG. 4(b). Variations in local signal power can be due to body movements (resulting in short peaks), but can also be due to changes in the lying position causing the amplitude of (in this case) the respiratory effort signal to increase considerably for a rather long interval (several minutes). The illustrative median removal filter 26 can be used to remove these "plateaus", leaving the short peaks intact. For each epoch i the filtered body motion estimation signal $e_f$ is given by:

$$e_f[i]=e[i]-\text{median}\{e[i-F], \ldots, e[i], \ldots, e[i+F]\} \qquad (9)$$

where F is half of the window size used for to compute the median.

FIG. 15 illustrates the effect of the median removal filter 26 on the local signal power illustrated in FIG. 4(b). FIG. 15 plots the accelerometer-based actigraphy signal (top plot), the body motion estimation by local signal power from respiratory effort (middle plot) and the body motion estimation signal after filtering by the median removal filter 26 (bottom plot). As it can be seen in FIG. 15, the "plateaus" caused by changes in the local signal power are almost completely removed, the only remaining component in those periods being a low-amplitude, high-frequency noise.

Additionally or alternatively, the high pass filter 28 can be used to remove the low frequency variation due to the local power variations while preserving the sharp, short peaks that correspond to body movements.

The illustrative examples are used to obtain the movement signal, but another use is that the movement signals are derived and then the original signals are enhanced using this movement signal. In its simplest embodiment the movement signal is used as an indication that the original biophysical signal is unreliable.

The disclosed actigraphy techniques are suitably employed in monitoring devices or situations in which measuring "real" actigraphy (e.g. with Actiwatch or another accelerometer-based actigraphy device) is not possible, or convenient. For example, the disclosed approaches can be used in conjunction with Holter Monitors.

The disclosed actigraphy techniques can be used to evaluate sleep (sleep/wake detection can be done reasonably well with actigraphy), or to measure the response/recovery of the heart to intense or prolonged periods of movement (typically corresponding to exercise or other sorts of activity).

The disclosed actigraphy techniques can be used to estimate actigraphy for sleep diagnostics devices such as the Stardust II Sleep Recorder (available from Koninklijke Philips N. V., Eindhoven, the Netherlands) which records respiratory effort. Such a device can be readily modified to incorporate the actigraphy synthesis module 20 so as to provide an additional modality (actigraphy) without the need to add a new sensor or modify the recording hardware (if the actigraphy synthesis module 20 is implemented off-device, for example in analysis software operating on data downloaded from the sleep recorder.

The disclosed actigraphy techniques can be used to estimate actigraphy for screening devices which typically comprise one or two modalities, such as the Philips RUSleeping RTS Screener (available from Koninklijke Philips N. V., Eindhoven, the Netherlands). Again, the actigraphy synthesis module 20 provides an additional modality without having to modify the hardware in order to add an additional sensor. Again, the actigraphy synthesis module 20 is optionally implemented off-device, for example in analysis software operating on downloaded data.

More generally, the disclosed actigraphy techniques can be used in the fields of monitoring and biosignal analysis, where having an additional actigraphy sensor is undesirably expensive (e.g., requiring the modification of the hardware of a sensor in order to add an accelerometer, and additional data logging capacity) or inconvenient (e.g., activity estimation typically requires a wrist-worn device, which has to be worn by the user in addition to whatever other sensors are used for monitoring purposes).

It will also be appreciated that the actigraphy synthesis module 20 may be physically embodied as a non-transitory storage medium storing instructions that are readable and executable by an electronic data processing device (e.g. a microprocessor, microcontroller, computer, et cetera) to perform the disclosed operations, e.g. operations 22, 24 optionally along with operations 26 and/or 28. The non-transitory storage medium may, for example comprise a flash memory, a read-only memory (ROM), programmable read-only memory (PROM), a hard disk drive or other magnetic storage medium, an optical disk or other optical storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A physiological monitoring device comprising:
    a sensor configured to generate a non-body motion physiological parameter signal as a function of time for a physiological parameter other than velocity, displacement, and acceleration; and
    an electronic digital signal processing (DSP) device configured to perform operations including:
        computing a body motion artifact (BMA) signal as a function of time from the non-body motion physiological parameter signal, and
        computing an actigraphy signal as a function of time from the BMA signal.

2. The physiological monitoring device of claim 1 wherein the sensor includes an electrocardiography (ECG) sensor and the physiological parameter includes one or more of (i) at least one ECG trace and (ii) a heart rate.

3. The physiological monitoring device of claim 1 wherein the sensor includes a respiratory sensor and the physiological parameter includes a respiration rate.

4. The physiological monitoring device of claim 1 wherein the sensor includes a Respiratory Inductive Plethysmography (RIP) sensor.

5. The physiological monitoring device of claim 1 wherein computing a BMA signal as a function of time from the non-body motion physiological parameter signal comprises computing a local signal power signal from the non-body motion physiological parameter signal.

6. The physiological monitoring device of claim 1 wherein computing a BMA signal as a function of time from the non-body motion physiological parameter signal comprises computing a local signal variance signal from the non-body motion physiological parameter signal.

7. The physiological monitoring device of claim 1 wherein computing a BMA signal as a function of time from the non-body motion physiological parameter signal comprises computing a Short-Time Fourier Transform (STFT) signal from the non-body motion physiological parameter signal.

8. The physiological monitoring device of claim 1 wherein computing a BMA signal as a function of time from the non-body motion physiological parameter signal comprises computing a wavelet transform signal from the non-body motion physiological parameter signal.

9. The physiological monitoring device of claim 1 wherein computing a BMA signal as a function of time from the non-body motion physiological parameter signal comprises computing a BMA signal sample for each time window of a succession of time windows of the non-body motion physiological parameter signal.

10. The physiological monitoring device of claim 9 wherein the succession of time windows is a succession of overlapping Hamming time windows.

11. The physiological monitoring device of claim 1 wherein computing an actigraphy signal as a function of time from the BMA signal comprises applying a linear transform to the BMA signal.

12. The physiological monitoring device of claim 1 wherein the DSP device is configured to perform further operations including:
    filtering the actigraphy signal using a median removal filter.

13. The physiological monitoring device of claim 1 wherein the DSP device is configured to perform further operations including:
    filtering the actigraphy signal using a high pass filter.

14. A non-transitory storage medium storing instructions readable and executable by an electronic data processing device to perform a physiological monitoring method comprising:
    computing a body motion artifact (BMA) signal comprising one of a local signal power signal, a local signal variance signal, a Short-Time Fourier Transform (STFT) signal, and a wavelet transform signal as a function of time from a non-body motion physiological parameter signal as a function of time for a physiological parameter other than displacement, acceleration, and velocity wherein a BMA signal sample is computed for each time window of a succession of time windows; and
    computing an actigraphy signal as a function of time from the BMA signal.

15. The non-transitory storage medium of claim 14, wherein the operation of computing a BMA signal as a function of time from the non-body motion physiological parameter signal comprises one of:
    computing a local signal variance signal from the non-body motion physiological parameter signal;
    computing a Short-Time Fourier Transform (STFT) signal from the non-body motion physiological parameter signal; and
    computing a wavelet transform signal from the non-body motion physiological parameter signal.

16. The non-transitory storage medium of claim 14, wherein the operation of computing a BMA signal as a function of time from the non-body motion physiological parameter signal comprises computing a BMA signal sample for each time window of a succession of time windows of the non-body motion physiological parameter signal.

17. The non-transitory storage medium of claim 14, wherein the instructions further include:
    filtering the actigraphy signal using a median removal filter or a high pass filter, wherein the filtering operation is performed by the electronic data processing device.

18. A physiological monitoring device comprising:
    at least one of an electrocardiography (ECG) sensor and a respiratory sensor configured generate a non-body motion physiological parameter signal as a function of time, the physiological parameter signal including at least one of a heart rate signal, at least one ECG trace signal, and a respiration rate signal; and
    at least one processor programmed to:
        compute a body motion artifact (BMA) signal as a function of time from the non-body motion physiological parameter signal;

applying a linear transform to the BMA signal;
compute an actigraphy signal as a function of time from the applied linear transform BMA signal.

19. The device of claim 18, wherein the at least one processor is programmed to compute the BMA signal as a function of time from the non-body motion physiological parameter signal by one of:
  computing a local signal variance signal from the non-body motion physiological parameter signal;
  computing a Short-Time Fourier Transform (STFT) signal from the non-body motion physiological parameter signal; and
  computing a wavelet transform signal from the non-body motion physiological parameter signal.

20. The device of claim 18, wherein the at least one processor is programmed to compute the BMA signal as a function of time from the non-body motion physiological parameter signal by:
  computing a BMA signal sample for each time window of a succession of time windows of the non-body motion physiological parameter signal.

* * * * *